United States Patent [19]
Suzuki

[11] 4,238,758
[45] Dec. 9, 1980

[54] SEMICONDUCTOR GAS SENSOR
[75] Inventor: Shunji Suzuki, Suwa, Japan
[73] Assignee: Kabushiki Kaisha Suwa Seikosha, Tokyo, Japan
[21] Appl. No.: 967,816
[22] Filed: Dec. 8, 1978
[30] Foreign Application Priority Data
  Dec. 8, 1977 [JP] Japan .................. 52-147492
[51] Int. Cl.³ .......................................... H01L 29/66
[52] U.S. Cl. ......................................... 357/25; 357/23
[58] Field of Search ..................................... 357/23, 25
[56] References Cited
U.S. PATENT DOCUMENTS
  3,832,700  8/1974  Wil .......................................... 357/23

OTHER PUBLICATIONS
Jour. App. Physics–vol. 46, No. 9, Sep. 1975, Lundstrom et al., pp. 3876–3881.

Primary Examiner—Edward J. Wojoiechowicz
Attorney, Agent, or Firm—Blum, Kaplan, Friedman, Silberman & Beran

[57] ABSTRACT

A metal-oxide-semiconductor transistor gas sensor including a gate oxide film of a dielectric material having a permittivity of more than about ten between a substrate and a gate is provided. The existence of a particular gas is detected by the change in threshold voltage of the transistor.

11 Claims, 1 Drawing Figure

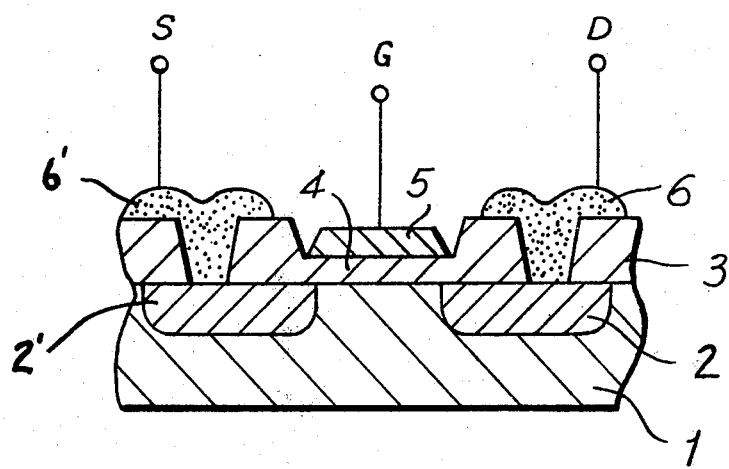

SEMICONDUCTOR GAS SENSOR

BACKGROUND OF THE INVENTION

This invention relates generally to an improved gas sensor, and in particular to an improved gas sensor which detects the presence of gas by the change in threshold voltage of a MOS transistor.

Recently, highly accurate, inexpensive gas sensors have become popular and several have been commercialized. These gas sensors have been used for the purpose of detecting the presence of gas in order to prevent a gas explosion. They also have been used in homes or public establishments to indicate existence of a fire. In these situations the gas sensors is relied upon to determine the presence of gas. A defective sensor can cause an accident. Thus, a highly accurate sensor is required. Further, in veiw of the popularization of the gas sensors for home use, a relatively inexpensive gas sensor is desired.

Having these objectives in mind, the following types of conventional gas sensors have been available. First, a detector was based on combustion of a gas utilizing platinum as a catalyst. This type of detector deteriorated with time as the catalyst deteriorated and the gas alarm could not be generated unless the gas concentration is maintained. In addition, the detecting voltage is extremely low, so that a complicated bridge circuit is required in this type of detector. This results in an expensive detector and further it is not possible to select a gas to be detected.

Another type of detector utilized to overcome these short comings utilizes a sintered metal-oxide-semiconductor. This type of detector is highly sensitive to gases and a simplified circuit structure can be used therein. However, since the sensor element generally must be heated up to a temperature of several hundred degrees centigrade in order to improve the sensitivity, the electric power consumption is considerably high. In addition, the stability of the sensor element is also subject to some deterioration with time. As with the platinum catalyst detectors, the problem of a lack of ability to select a gas to be detected has not been overcome.

Alternatively, a detector may be based on using a photoelectric method or a smoke sensor may be based on an ionization method. However, both methods are poor in their ability to distinquish the gas to be detected, are large and bulky in size. In the latter or ionization type of smoke sensor, a radioisotope is utilized as an ionization source raising the question that the radiation may be harmful to humans.

Recently, a gas sensor utilizing a MOS transistor in a new method has been proposed as an alternative to the above-noted methods. This is to say, by employing a material which absorbs gases and is sensitive thereto as a gate electrode of the transistor, the change in threshold voltage due to the existence of the gas is detected. In this method, the sensor element can be massproduced inexpensively by known IC manufacturing techniques. In addition, a sensor element of high quality and uniform properties can be readily manufactured. Moreover, the sensor element can be miniturized, so that a driving circuit can be formed on the same substrate and the power consumption can be reduced.

The only shortcoming in this new method is that the sensor element utilized is not sensitive to gases because a heating member which can be utilized in other methods cannot be employed in the MOS method in view of the deleterious long term effects on the reliability of the MOS transistor. Accordingly, it is desirable to provide a MOS transistor gas sensor having sufficient sensitivity to gases at room temperature so as to be practical. The gas is detected by examining the relationship between the absorption of gases and the threshold voltage change in a MOS. A highly sensitive sensor can be provided when the threshold voltage change due to absorption and desorption of the gases is extremely large.

SUMMARY OF THE INVENTION

Generally speaking, in accordance with the invention, a metal-oxide-semiconductor transistor gas sensor having improved sensitivity to gases at room temperature is provided. The presence of gas is detected by the change in threshold voltage of the field effect MOS transistor. The gas sensor includes a gate oxide film of permittivity of more than about ten between the gate and the substrate.

Accordingly, it is an object of the invention to provide an improved gas sensor.

Another principal object of the invention is to provide an improved semiconductor gas sensor for detecting the existence of a certain gas by the change in threshold voltage of a MOS transistor.

A further principal object of the invention is to provide an improved miniturized gas sensor which is highly accurate.

Still another object of the invention is to provide an improved semiconductor gas sensor wherein a dielectric film having dielectric permittivity of more than about ten between a silicon substrate and a metal gate.

Still other objects and advantages of the invention will in part be obvious and will in part be apparent from the specification.

The invention accordingly comprises the several steps and the relation of one or more of such steps with respect to each of the others, and the article possessing the features, properties, and the relation of elements, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawing, in which:

The sole FIGURE is a cross-sectional view showing a semiconductor gas sensor constructed and arranged in accordance with the invention.

DESCRIPTION OF THE PREFERRED EMBODIMENTS

Referring now to the FIGURE, a cross-sectional view of a field effect metal-oxide-semiconductor transistor gas sensor which may be employed for detecting hydrogen gas is shown. A first surface of the gas sensor includes a silicon substrate 1 having a pair of spaced apart diffusion regions 2 and 2'. A gate oxide film 4 is disposed on the first surface of substrate 1 in contact with a portion of the remaining surface of diffusion layers 2 and 2'. A palladium gate electrode 5 is disposed on gate oxide film 4 in the region between diffusion regions 2 and 2'. A chromium-gold plug 6 is located in each region on the surface of substrate 1 in contact with diffusion regions 2 and 2' free of field oxide film 3 and gate oxide film 4 for electrically connecting a lead wire 7 thereto. A drain lead wire D is electrically connected through plug 6 to drain diffusion region 2 and a source lead wire S is electrically connected through plug 6' to source diffusion region 2'. A gate lead wire G is electrically connected directly to gate electrode 5.

In a MOS transistor for detecting hydrogen gas as shown in the FIGURE, when hydrogen is absorbed on and diffuses into gate electrode 5 a polarized region is formed on the boundary surface between gate oxide film 4 and substrate 1. At this time the work-function of gate electrode 5 changes thereby changing the threshold voltage. This change in threshold voltage is measured to determine presence of the hydrogen.

Generally, in a MOS transistor illustrated in the FIGURE, a silicon wafer is employed as substrate 1, silicon dioxide as gate oxide film 4 and palladium as gate electrode 5. However, by utilizing these materials in a gas detecting sensor, the polarization of the boundary surface is between gate oxide film 4 and the substrate 1 caused by the absorption and desorption of hydrogen gas occurs slowly. Thus, the changes in threshold voltage are extremely small and it is fairly difficult to utilize this type of sensor in a commercial gas sensor.

In accordance with the invention, dielectric substances are utilized in place of the conventional silicon dioxide film in order to obtain a large change in the threshold voltage and the work-function. Specifically, a silicon dioxide film has a dielectric permittivity of from 4 to 7 and has been utilized conventionally. In contrast thereto, in accordance with the invention, a titanium dioxide-magnesium oxide film having a permittivity of from about 18 to 25 and a titanium dioxide film having a permittivity of from about 70 to 85 are utilized for gate oxide film 4. These gas sensor elements are extremely sensitive to hydrogen gas when compared with conventional sensor elements are obtained. While a conventional sensor element can detect hydrogen gas present in amounts ranging from 200 to 300 ppm, a sensor element constructed and arranged in accordance with the invention can detect hydrogen gas present in amounts as low as from about 50 to 80 ppm. Moreover, the change in threshold voltage due to absorption and desorption of the gas occurs immediately, whereby a sensitivity to gases much higher than can be obtained in conventional elements is obtained. The increased sensitivity to gases may be obtained by employing as a gate oxide film of the conventional MOS transistor, various oxides, nitrides, sulfides and other compounds having a dielectric permittivity of more than about 10.

In another embodiment of the invention, a gas sensor having the structure shown in the FIGURE includes gate oxide film 4 of a dielectric substance, such as barium titanate ($BaTiO_3$). The barium titanate film is formed between gate 5 and substrate 1 by the reactive sputtering process. The permittivity of the barium titanate film is in the range of from about 620 to 1100 and the sensitivity to gases approaches ten times to one hundred and several tens times that of the conventional gas sensor elements. In the FIGURE, gate electrode wire G is provided, however, in a gas sensor wherein special dielectric film is included, gate 5 may be floated electrically allowing elimination of gate electrode wire G.

The semiconductor gas sensor constructed and arranged in accordance with the invention has been described above with respect to detection of hydrogen gas. Other combustible gases, for example, carbon monoxide, oxygen and ozone can also be readily detected by selecting an appropriate substance to be utilized as the gate electrode. In these cases, the transistor gas sensor may include $SnO_2$, $ZnO$ or $Fe_2O_3$ in place of a metal as the gate material.

As noted above, in a gas sensor including a MOS transistor constructed and arranged in accordance with the invention a dielectric film having high permittivity is formed between the gate and the substrate for providing a gas sensor which is highly sensitive to gases and provides immediate responses. Accordingly, by constructing the gas sensor in accordance with the invention, it is possible to provide a highly accurate and inexpensive gas sensor of high reliability in comparison to the conventional gas sensors utilizing platinum or the sintered metal-oxide-semiconductor materials.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A metal-oxide-semiconductor transistor gas sensor comprising:
    a semi-conductive substrate of given conductivity type;
    at least two spaced apart diffusion regions in said substrate, said diffusion regions formed from a dopant material having a conductivity opposite from said substrate;
    a field oxide film disposed on the surface of said substrate contacting at least a portion of the surface of each of said diffusion regions;
    a gate oxide film comprising an oxide semiconductor having a work-function dependent upon absorption of gas, said gate oxide film disposed on the surface of said substrate at the region free of said dopant material and contacting at least a portion of the remaining surface of each of said diffusion regions, said gate oxide film having a permittivity of more than 10;
    a gate disposed on said gate oxide film; and
    contact means for connecting said spaced apart diffusion regions and said gate electrode to external circuitry for detecting said charge in work-function of said gate oxide film.

2. The gas sensor of claim 1, wherein said contact means includes a metal electrode in contact with the surface of each said diffusion region free of oxide film for providing electrical connection to said diffusion regions and an electrode in contact with said gate.

3. The gas sensor of claim 1 for detecting hydrogen, wherein said gate is palladium and said gate oxide film is a dielectric film for providing a large change in threshold voltage in the presence of hydrogen.

4. The gas sensor of claim 3, wherein said dielectric film comprises titanium dioxide of permittivity of between about 70 and 85.

5. The gas sensor of claim 3, wherein said dielectric film is titanium dioxide-magnesium oxide of permittivity between about 18 and 25.

6. The gas sensor of claim 3, wherein said dielectric film is a barium titanate film of permittivity of between about 620 and 1100.

7. The gas sensor of claims 4, 5 or 6, wherein said contact means includes a metal electrode in contact with the surface of each said diffusion region free of oxide film for providing electrical connection to said diffusion regions and a metal electrode in contact with said gate.

8. The gas sensor of claim 7 wherein said electrodes are chromium-gold.

9. The gas sensor of claim 1, wherein said gate material is tin oxide.

10. The gas sensor of claim 1, wherein said gate material is zinc oxide.

11. The gas sensor of claim 1, wherein said gate material is ferric oxide.

* * * * *